United States Patent

Honda et al.

[11] Patent Number: 5,139,952
[45] Date of Patent: Aug. 18, 1992

[54] TISSUE CULTURE FLASK

[75] Inventors: Shinzo Honda, Honmachi; Jiro Akiyama, Yotsukaido; Takeshi Yamamoto, Kiyose, all of Japan

[73] Assignee: Terumo Corporation, Tokyo, Japan

[21] Appl. No.: 728,048

[22] Filed: Jul. 8, 1991

Related U.S. Application Data

[63] Continuation of Ser. No. 374,580, Jul. 3, 1989, abandoned, which is a continuation of Ser. No. 852,206, Apr. 15, 1986, abandoned.

[51] Int. Cl.$^5$ .......................... C12M 3/00; C12M 1/24
[52] U.S. Cl. .................................... 435/284; 435/285; 435/296; 422/102
[58] Field of Search ............... 435/284, 285, 296, 297, 435/298, 299, 300, 301; 422/102; 215/6, 31

[56] References Cited

U.S. PATENT DOCUMENTS

| | | |
|---|---|---|
| 2,947,116 | 8/1960 | Earle et al. ...................... 435/285 X |
| 3,449,210 | 6/1969 | Rohde ................................ 435/296 |
| 3,870,602 | 3/1975 | Froman et al. |
| 4,334,028 | 6/1982 | Carver ............................. 435/285 X |
| 4,770,854 | 9/1988 | Lyman ................................ 435/296 |

FOREIGN PATENT DOCUMENTS 0141104 5/1985 European Pat. Off. ............ 435/296

60-70067 4/1985 Japan .

Primary Examiner—Robert J. Warden
Assistant Examiner—William H. Beisner
Attorney, Agent, or Firm—Burns, Doane, Swecker & Mathis

[57] ABSTRACT

A tissue culture flask includes a container main body comprising a box having a bottom surface for supporting a substance to be cultured, a side surface, and an upper surface. A cylindrical neck is provided on the side surface of the container main body to communicate with the interior of the container main body, and extends obliquely upward with respect to the bottom surface and defining a first opening at an end located away from the container main body and a second opening opposite the first opening. In the flask, (1) a first angle defined by (a) a first straight line connecting a given point on the bottom surface including an edge thereof and a given point on an edge of the first opening and (b) a second straight line on the inner circumferential wall and connecting a given point on an edge of the first opening and a given point on an edge of the second opening is not greater than (2) a second angle defined by (c) said second straight line and (d) the longest third straight line connecting a given point on an edge of the first opening and a given point on an edge of the second opening.

2 Claims, 5 Drawing Sheets

TISSUE CULTURE FLASK

This application is a continuation of application Ser. No. 07/324,580, filed July 3, 1989, now abandoned which is a continuation of application Ser. No. 06/852,206 filed on Apr. 15, 1986 now abandoned.

BACKGROUND OF THE INVENTION

1. Field of the Invention

The present invention relates to a tissue culture flask for tissue culture, from which a cultured tissue can be recovered by a rod-like recovering means.

2. Description of the Prior Art

Tissue culture flasks are used to culture cells, tissues, organs and so on in vitro. Tissue culture flasks which can be stacked and which are of as small a size as possible are required for convenience in maintenance. A conventional small-sized culture flask is shown in FIGS. 1 to 3.

As shown in FIGS. 1 to 3, conventional tissue culture flask 10 consists of container main body 2 and neck 3. Main body 2 is a box having flat bottom surface 21 and a substantially rectangular-parallelepiped interior. Front side surface 22 of main body 2 consists of inclined lower surface 221 contiguous with surface 21, oblique side surfaces 222 and 223 contiguous with right-side surface 23 and left-side surface 24, respectively, and major surface 224 contiguous with surfaces 221, 222 and 223 and located at the front-most portion of main body 2. Neck 3 having container port 35 is integrally formed with surface 224 of surface 22 of main body 2 and extends obliquely upward with respect to surface 21.

In conventional flask 10, a distal end of pipette P or a scraper cannot reach the inner edge of surface 21 at a side of port 35 (see FIG. 2). Therefore, not all the cells attached to surface 21 in the inner surface of flask 10 can be recovered from port 35. That is, cells in some area (hatched portion in FIG. 2) cannot be removed, resulting in inconvenience.

SUMMARY OF THE INVENTION

The present invention has been made in view of the above situation and has as its major object to provide a tissue culture flask having a shape that allows a distal end of a pipette or a scraper inserted from its container port to reach its entire bottom surface area.

The tissue culture flask of the present invention comprising a container main body comprising a box having a bottom surface for supporting a substance to be cultured, a side surface and an upper surface, and a hollow cylindrical neck provided on the side surface of the container main body to communicate with the interior of the container main body, extending obliquely upward with respect to the bottom surface and defining a first opening at a distal end thereof and a second opening at a proximal end thereof. In the flask, (1) a first angle defined by (a) a first straight line connecting a given point on the bottom surface including an edge thereof and a given point on an edge of the first opening and (b) a second straight line on the inner circumferential wall and connecting a given point on an edge of the first opening and a given point on an edge of the second opening is not greater than (2) a second angle defined by (c) said second straight line and (d) the longest third straight line connecting a given point on an edge of the first opening and a given point on an edge of the second opening. Thus, a linear rod-like member inserted in the container main body from the neck can reach any point on the bottom surface of the container main body (including its edge).

BRIEF DESCRIPTION OF THE DRAWINGS

FIGS. 1 to 3 show a structure of a conventional tissue culture flask, in which:

FIG. 1 is a left-side view;

FIG. 2 is a bottom view; and

FIG. 3 is a front view.

FIGS. 4 to 8 show an embodiment of the present invention, in which:

FIG. 4 is a plan view;

FIG. 5 is a left-side view;

FIG. 6 is a sectional view taken along the line VI—VI of FIG. 4;

FIG. 7 is a bottom view; and

FIG. 8 is a front view.

FIGS. 9 to 11 show another embodiment of the present invention, in which:

FIG. 9 is a left-side view;

FIG. 10 is a bottom view; and

FIG. 11 is a front view.

FIGS. 12 to 14 show another embodiment of the present invention, in which:

FIG. 12 is a left-side view; FIG. 13 is a bottom view; and

FIG. 14 is a front view.

DETAILED DESCRIPTION OF THE PREFERRED EMBODIMENTS

Figure 1:
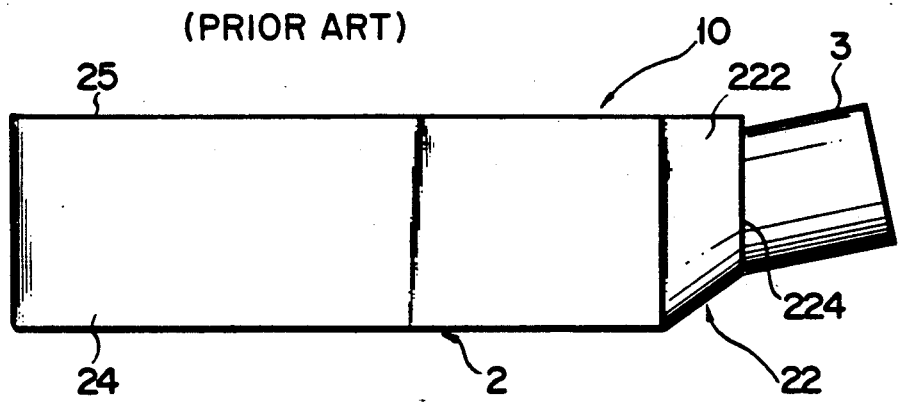

The structure of the flask of the present invention will be described in detail with reference to the accompanying drawings.

FIGS. 4 to 8 show a first embodiment of the present invention.

Referring to FIGS. 4 to 8, container main body 2 of tissue culture flask 1 consists of bottom surface 21, normally flat right- and left-side surfaces 23 and 24, upper surface 25, rear side surface 26 and front side surface 22. A side of surface 21 facing the interior of main body 2 is a flat surface.

A space at a rear portion of the container defined by surfaces 21, 23, 24, 25 and 26 preferably has a substantially rectangular parallelpiped shape, as shown in the drawings. With this shape, flasks 1 can be stacked, can have a small size, and can minimize an error between a required amount of culture medium to be supplied and the amount of the medium actually supplied.

Surface 21 must be flat since it carries the culture medium contained in flask 1. Alternatively, surface 21 preferably has a polygonal shape defined by substantially linear lines with round corners. With such a structure, the area defined by surface 21 can be correctly determined, resulting in accurate culturing.

Figure 7:
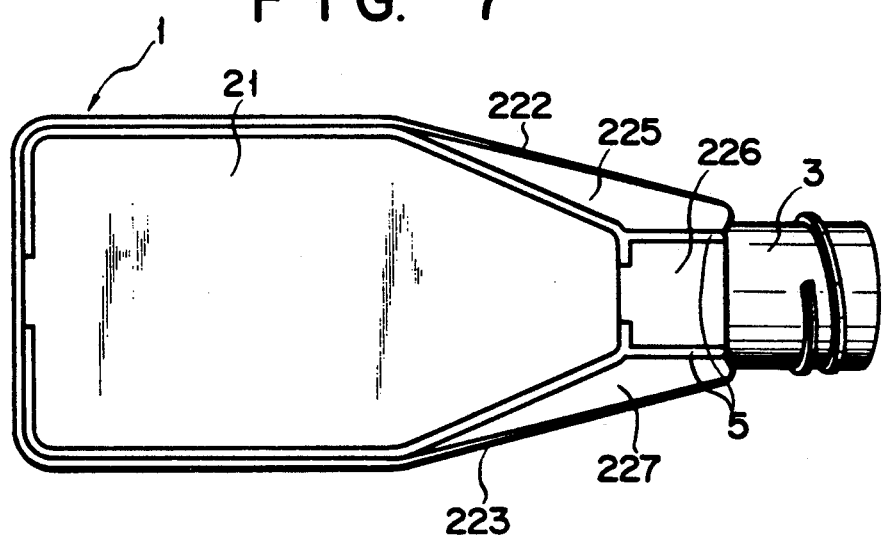
Figure 8:
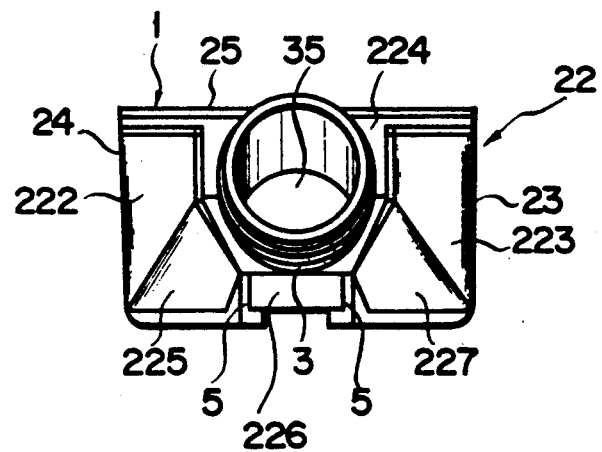

Since the rear portion of surface 21 has a U-shape, surface 21 normally has five or more corners and is preferably a hexagon, as shown in FIG. 7.

Since bottom surface 21 of a conventional flask has a rectangular shape (see FIG. 2), a pipette inserted from container port 35 cannot reach either of the two front corners of surface 21. However, if the two corners are cut so that surface 21 is a pentagon or a polygon having 5 or more corners (preferably a hexagon), when the interior of main body 2 is viewed from port 35 in varying directions by a human eye, all of the edges of surface 21 can be visually observed through port 35, thereby allowing the pipette or the like to easily reach all fillet portions.

When surface 21 is a polygon having five or more corners, front side surface 22 preferably consists of an oblique side surface, an inclined lower surface, and a major surface contiguous with neck 3, extending obliquely upward with respect to surface 22.

In FIG. 7, surface 21 is a hexagon. Accordingly, surface 22 consists of three inclined lower surfaces 225, 226 and 227 contiguous with the front linear edge of surface 21, major surface 224, and with each other, and two oblique side surfaces 222 and 223. Surface 222 is contiguous with surfaces 225, 24, 21 and 224. Surface 223 is contiguous with surfaces 227, 23, 21 and 224.

In this case, it is apparent that inclined lower surfaces can be provided in accordance with the number of sides in the polygon formed by the bottom surface. When the number of sides of the polygon is n (n≧5), the number of the inclined lower surfaces is n−3.

Cylindrical neck 3 having port 35 is integral with surface 224 and extends obliquely upward with respect to surface 21. Thus, the area of surface 224 integral with neck 3 can be so reduced that it is negligible.

With this configuration, according to the first aspect of the present invention, when the interior of main body 2 is viewed from port 35, all the edges of bottom 21 can be seen directly. More specifically, referring to FIG. 6, angle $\theta_1$ defined by straight line L1 connecting point P1 on a front end of an opening of cylindrical neck 3 and point P2 on a rear end of an opening thereof, and a circumferential wall surface of neck 3 is larger than angle $\theta_2$ defined by straight line L2 connecting point P1 and given point P3 on an edge of surface 21 and the circumferential wall surface of neck 3. This allows a rod-like recovery means to reach all of the edges of surface 21 with its distal end.

When legs 5 are provided to the bottom portion of flask 1, stability of flask 1 is increased.

Figure 9:
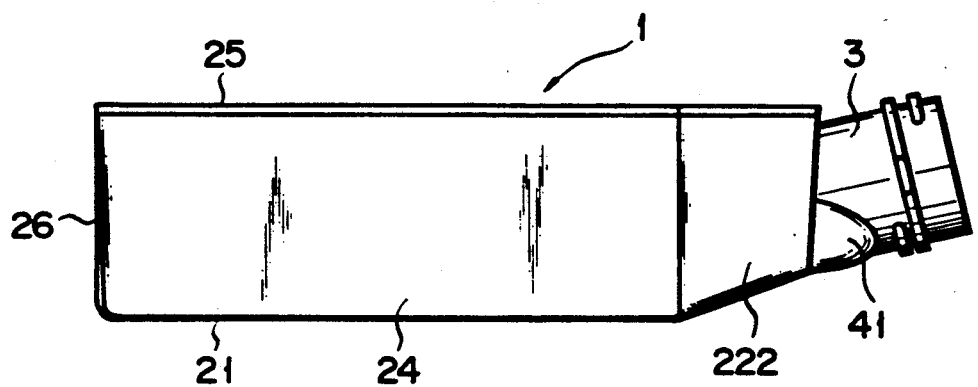
Figure 10:
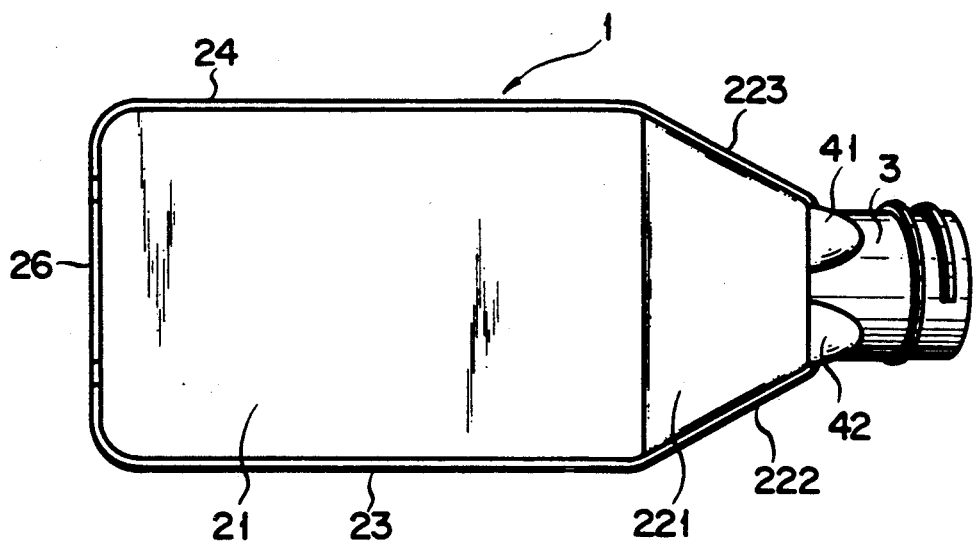
Figure 11:
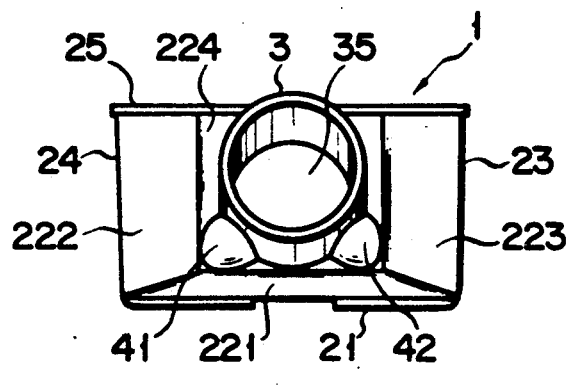

FIGS. 9 to 11 show another embodiment according to a second aspect of the present invention.

Figure 2:
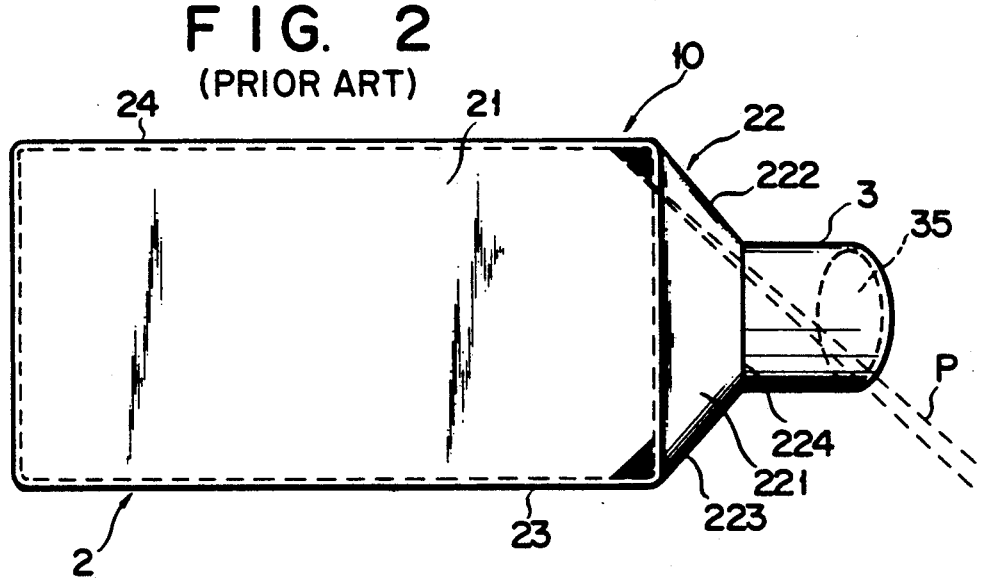
Figure 3:
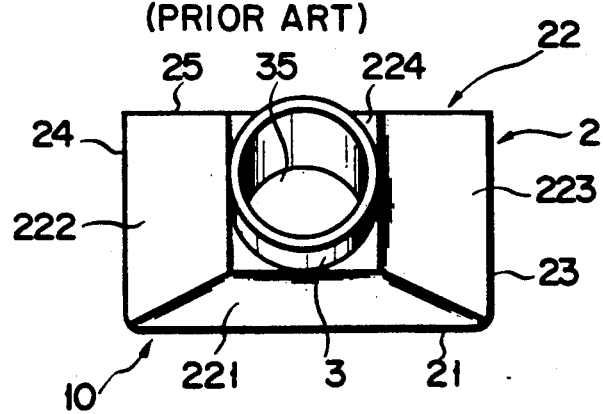
Figure 4:
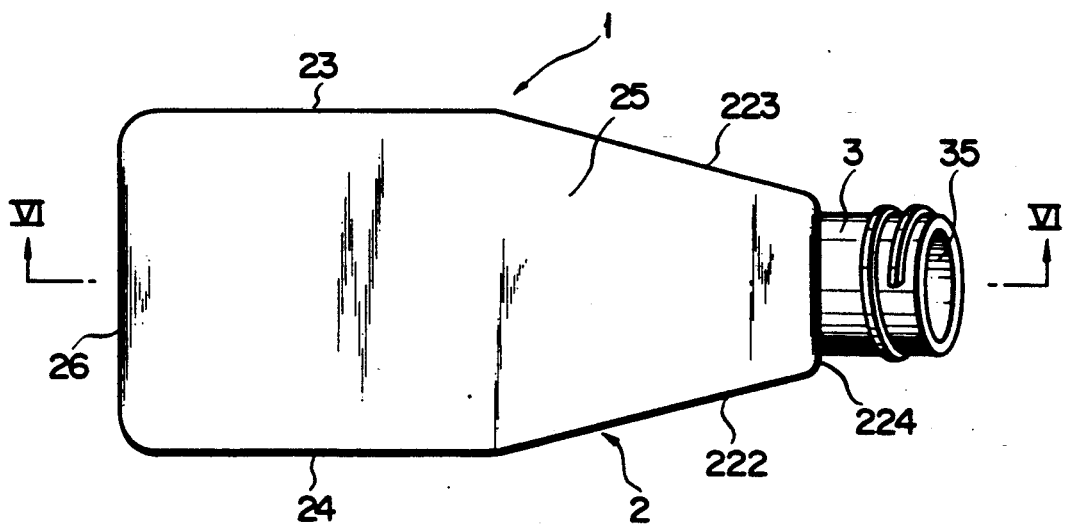
Figure 5:
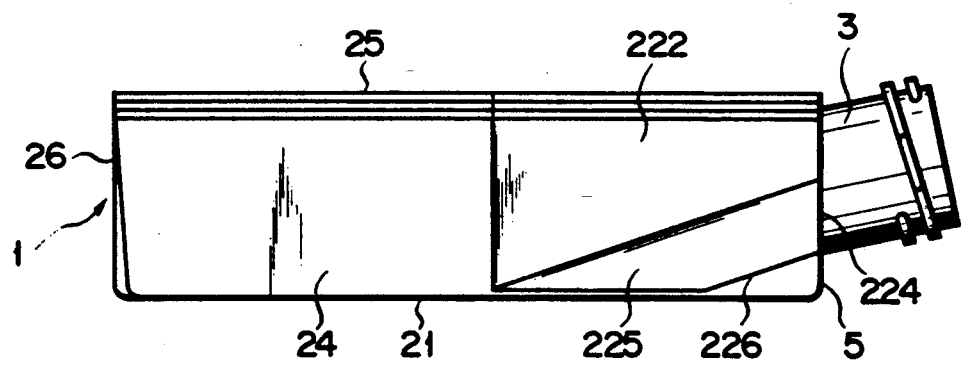
Figure 6:
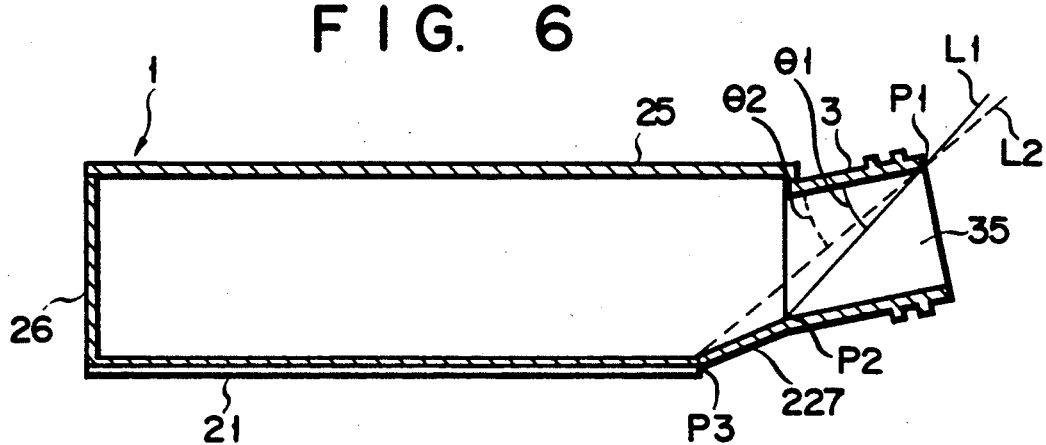

In FIGS. 9 to 11, unlike the conventional flask shown in FIGS. 1 to 3, curved portions 41 and 42 which project outward from main body 2 are provided on a contiguous portion of major surface 224 and neck 3.

Portions 41 and 42 are two separate curved surfaces or constitute a single curved portion obtained by connecting two curved surfaces at a contiguous portion of surface 224 and neck 3 having port 35. With portions 41 and 42, the entire area of front corners of surface 21 can be seen directly through port 35, so that a linear pipette or the like can reach them.

Figure 12:
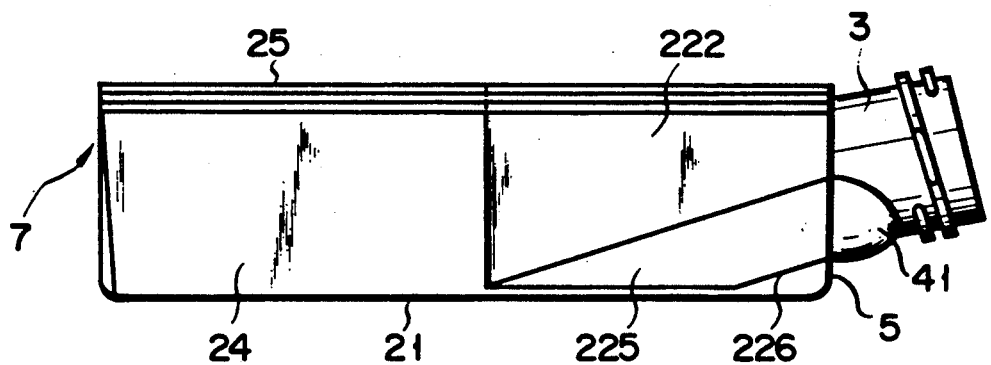
Figure 13:
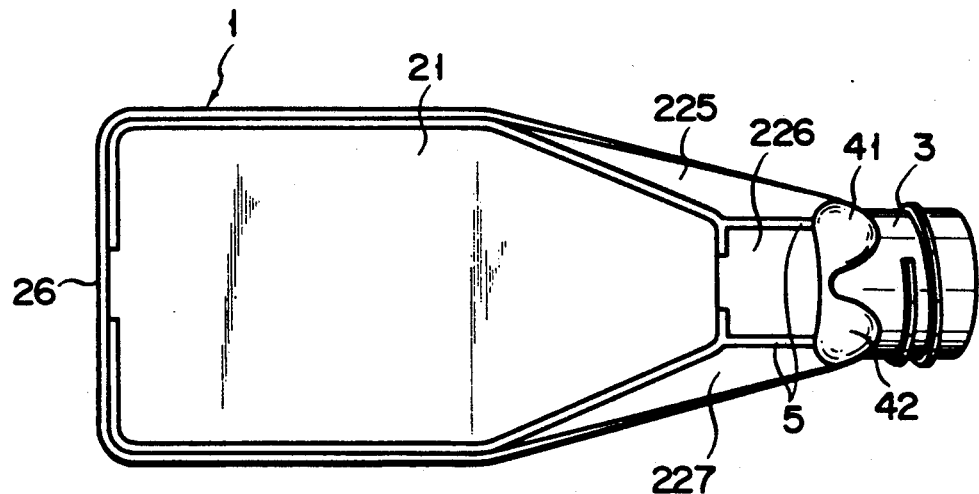
Figure 14:
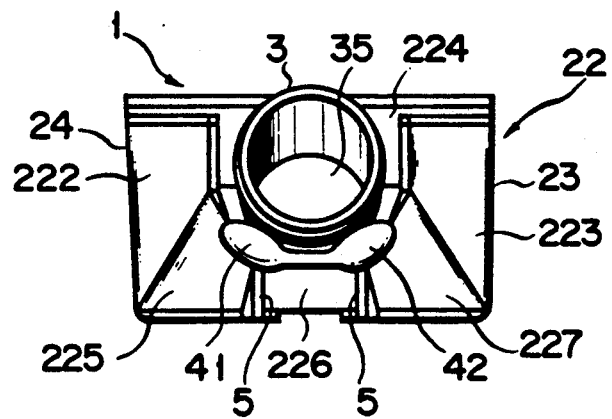

FIGS. 12 to 14 show still another embodiment according to a third aspect of the present invention obtained by combining the first and second aspects described above.

In FIGS. 12 to 14, curved portions 41 and 42, which project outward from main body 2, are provided on a contiguous portion of surface 224 and neck 3 of the flask shown in FIGS. 4 to 8.

When the second aspect is combined with the first aspect in this manner, a pipette or the like can reach any corner of the flask even if the inclinations of surfaces 225, 226 and 227 are steeper. Therefore, this enables size reduction and larger capacity in the tissue culture flasks.

The tissue culture flask of the present invention can be manufactured by forming a plurality of portions from a transparent material such as polystyrene, methacrylate resin, polycarbonate and polyethylene, and fusing them.

More particularly, a tissue culture flask of the present invention can be manufactured by separately forming a container main body including neck 3 (excluding upper surface 25), and upper surface 25, and fusing them.

In accordance with another manufacturing method, a tissue culture flask of the present invention can be manufactured by separately forming a container main body (excluding rear side surface 26 and containing neck 3 and surface 25), and rear side surface 26, and fusing them.

According to the present invention, a pipette or the like can reach all the edges of the bottom surface of the tissue culture flask, so that a recovery efficiency of cells and so on attached to the bottom of the flask can be greatly increased.

According to the first aspect of the present invention, the flasks can be stacked, the overall size is compact, and the required supply amount of culture medium can be easily discriminated from the depth of the culture liquid actually supplied.

According to the second aspect of the present invention, the area of the bottom surface of the flask can be determined correctly, and culturing, handling of the flask for analysis, and manufacture of the flask are easy.

According to the third aspect of the present invention, the effect of the present invention can be obtained by only slightly modifying the shape of a conventional tissue culture flask. Thereby, the amount of culture medium that is not removed upon decantation of the culture is decreased. When the third aspect of the present invention is combined with the second aspect, the inclination of the inclined lower surface of the front side surface can be increased. As a result, reduction in size and larger capacity of the flask and a decrease in the number of cells attached to the inclined bottom surface thereof can be enabled, and accidental out flow of the culture medium due to vibration can be prevented.

What is claimed is:

1. A tissue culture flask comprising:
    a container main body having an interior for holding a substance to be cultured, said main body including a bottom surface defined by a plurality of edges which are arranged in a shape having n corners, wherein n is an integer and n≧5, a rear side surface contiguous with said bottom surface, a right side surface contiguous with said bottom surface and said rear side surface, a left side surface contiguous with said bottom surface and said rear side surface, an upper surface positioned opposite said bottom surface, wherein said upper surface has n corners and is contiguous with said rear side surface, said left side surface and said right side surface, a major surface positioned opposite said rear side surface, n−3 inclined lower surfaces, each of said inclined lower surfaces being contiguous with said bottom surface, with said major surface and with at least one of said other inclined lower surfaces, and two oblique side surfaces, one of said oblique side surfaces being obliquely positioned with respect to and being contiguous with said left side surface, said major surface and one of said inclined lower surfaces and the other of said oblique side surfaces being obliquely positioned with respect to and being contiguous with said right side surface, said major surface and another of said inclined lower surfaces; and a neck provided on said major surface, said neck being hollow and communicating with the interior of the main body, said neck extending obliquely upwardly with respect to the bottom surface and having a first opening at a first end thereof located away from said main body and a second opening at a second end thereof opposite said first end, wherein (1) a first angle defined by (a) a first straight line connecting a given point on one of the edges of the bottom surface and a given point on an edge of the first opening and (b) a second straight line lying along an inner circumferential wall of the neck and connecting a given point on an edge of the first opening and a given point on an edge of the second opening is not greater than (2) a second angle defined by (c) said second straight line and (d) the longest third straight line connecting a given point on an edge of the first opening and a given point on an edge of the second opening, whereby a distal end of a linear pipette inserted through the cylindrical neck and into the container main body can contact the entire bottom surface including all of the edges and corners of the bottom surface.

2. The tissue culture flask according to claim 1, wherein said one oblique side surface intersects said left side surface at a first edge and said other oblique side surface intersects said right side surface at a second edge, an inner space of the main body defined by said bottom surface, said upper surface, said rear surface, said left side surface, said right side surface and a plane containing said first and second edges bieng a substantially rectangular parallelpiped.

* * * * *